(12) United States Patent
Proksa

(10) Patent No.: US 7,778,384 B2
(45) Date of Patent: Aug. 17, 2010

(54) DIRECT MEASURING AND CORRECTION OF SCATTER FOR CT

(75) Inventor: Roland Proksa, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/065,614

(22) PCT Filed: Sep. 1, 2006

(86) PCT No.: PCT/IB2006/053054

§ 371 (c)(1),
(2), (4) Date: Mar. 4, 2008

(87) PCT Pub. No.: WO2007/031898

PCT Pub. Date: Mar. 22, 2007

(65) Prior Publication Data

US 2008/0226020 A1   Sep. 18, 2008

(30) Foreign Application Priority Data

Sep. 13, 2005   (EP) ................... 05108406

(51) Int. Cl.
*A61B 6/00* (2006.01)
*G01N 23/00* (2006.01)
*G21K 1/12* (2006.01)
*H05G 1/60* (2006.01)
(52) U.S. Cl. ........................ 378/7; 378/98.4
(58) Field of Classification Search ............ 378/7, 378/98.4
See application file for complete search history.

(56) References Cited

U.S. PATENT DOCUMENTS

| 4,651,002 | A | | 3/1987 | Anno |
| 4,727,562 | A | * | 2/1988 | Belanger ............... 378/98.4 |
| 5,615,279 | A | * | 3/1997 | Yoshioka et al. ........... 382/131 |
| 6,639,964 | B2 | | 10/2003 | Schneider et al. |
| 7,396,162 | B1 | * | 7/2008 | Edic et al. ............... 378/207 |
| 2004/0091079 | A1 | | 5/2004 | Zapalac |
| 2004/0264629 | A1 | | 12/2004 | Tang |
| 2005/0025278 | A1 | | 2/2005 | Hagiwara |
| 2005/0147201 | A1 | | 7/2005 | Hoffman |
| 2006/0002509 | A1 | * | 1/2006 | Claus et al. ............... 378/21 |
| 2006/0062443 | A1 | * | 3/2006 | Basu et al. ............... 382/131 |

FOREIGN PATENT DOCUMENTS

DE   19953613 A1   5/2001
WO   WO 2004023123 A1 *   3/2004

* cited by examiner

*Primary Examiner*—Hoon Song
*Assistant Examiner*—Mona M Sanei

(57) ABSTRACT

Cone-beam CT scanners with large detector arrays suffer from increased scatter radiation. This radiation may cause severe image artefacts. An examination apparatus is provided which directly measures the scatter radiation and uses this measurement for a correction of the contaminated image data. The measurement is performed by utilizing a 1-dimensional anti-scatter-grid and an X-ray tube with an electronic focal spot movement. Image data is detected at a first position of a focal spot and scatter data is detected at a second position of the focal spot. The image data is corrected on the basis of the scatter data.

19 Claims, 3 Drawing Sheets

DIRECT MEASURING AND CORRECTION OF SCATTER FOR CT

The invention relates to the field of tomographic imaging. In particular, the invention relates to an examination apparatus for examination of an object of interest, to an image processing device, to a method of examination of an object of interest, a computer-readable medium and a program element.

Cone-beam CT scanners with large detector arrays suffer from increased scatter radiation. This radiation may cause severe image artefacts. In order to reduce image artefacts resulting from scatter radiation, two-dimensional anti-scatter-grids (ASG) may be used. However, it may be difficult to build such ASG's and the available production techniques are expensive. Furthermore, conventional two-dimensional anti-scatter-grids may not allow for advanced CT system concepts such as the so-called stereo-tube design.

It may be desirable to have an improved scatter correction.

According to an exemplary embodiment of the present invention, an examination apparatus for examination of an object of interest may be provided, the examination apparatus comprising a radiation source adapted for emitting electromagnetic radiation to the object of interest, a detector unit adapted for detecting image data and scatter data from the object of interest, and a correction unit adapted for correcting the image data on the basis of the scatter data, wherein the image data is detected at a first position of a focal spot of the electromagnetic radiation relative to the detector unit, and wherein the scatter data is detected at a second position of the focal spot relative to the detector unit, wherein the second position is different from the first position.

Therefore, scatter data may be acquired when the focal spot has been moved relative to the detector unit to a second position which is different from the (normal) first position of the focal spot (at which the image data is acquired). Thus, by moving the focal spot, two different data sets may be acquired, mainly the image data and (at a different position of the focal spot) the scatter data. This scatter data is then used for image correction.

According to another exemplary embodiment of the present invention, the examination apparatus further comprises an anti-scatter-grid adapted for filtering the electromagnetic radiation. For example, the anti-scatter-grid may be adapted such that no direct radiation hits the detector unit when the electromagnetic radiation is focussed to the second position of the focal spot.

Thus, the scatter data which is detected from the detector unit may comprise only little or even none direct radiation data.

According to another exemplary embodiment of the present invention, the anti-scatter-grid is a 1-dimensional anti-scatter-grid.

This may provide for an easy fabrication of the ASG. Furthermore, this may allow for the application for advanced CT system concepts such as stereo-tube design.

According to another exemplary embodiment of the present invention, the image data comprises a first amount of direct radiation and a second amount of scatter radiation. Furthermore, the scatter data comprises a third amount of direct radiation and a fourth amount of scatter radiation. Still further, a first fraction of the first amount and the second amount is significantly bigger than a second fraction of the third amount and the fourth amount.

Therefore, according to this exemplary embodiment of the present invention, the scatter data may only comprise a relatively small amount of direct radiation (which has not been scattered by the object of interest). Thus, by moving the focal spot for a scatter measurement the amount of direct radiation reaching the detector may be significantly reduced. Therefore, the resulting measurement (scatter data) may basically only contain scattered photons. Such a measurement may provide a good estimation of the scatter contribution to the imaging measurements.

According to another exemplary embodiment of the present invention, the radiation source is adapted for electronically moving the focal spot from the first position to the second position.

This may provide for a fast switching between the first position and the second position without mechanical movement.

According to another exemplary embodiment of the present invention, the image data is detected at a first time and the scatter data is detected at a second time, wherein the first time and the second time correspond to a detection sequence.

Therefore, according to this exemplary embodiment of the present invention, a detection sequence may be pre-determined. Then, during data acquisition, the focal spot is switched between the first position and the second position (for acquisition of image data and scatter data, respectively) according to the pre-determined detection or switching sequence. Since scatter may vary slowly in the spatial domain, the scatter measurements may only sporadically be interleaved in the image acquisition (according to the pre-determined detection sequence).

According to another exemplary embodiment of the present invention, the correction unit is further adapted for performing a first interpolation to substitute a missing imaging projection.

This may provide for an improved image quality.

According to another exemplary embodiment of the present invention, the correction unit is further adapted for performing a second angular interpolation to generate a scatter estimate for each projection angle.

This may further improve the image quality.

According to another exemplary embodiment of the present invention, the examination apparatus is further adapted for performing a low-pass filtering of the scatter data.

Therefore, high spatial frequencies of the scatter data may be blocked by the filter.

According to another exemplary embodiment of the present invention, the examination apparatus may be applied as a baggage inspection apparatus, a medical application apparatus, a material testing apparatus or a material science analysis apparatus. A field of application of the invention may be material science analysis, since the defined functionality of the invention may allow for a secure, reliable and highly accurate analysis of a material.

According to another exemplary embodiment of the present invention, the examination apparatus may further comprise a collimator arranged between the electromagnetic radiation source and the detector unit, wherein the collimator is adapted for collimating an electromagnetic radiation beam emitted by the electromagnetic radiation source to form a cone-beam.

Furthermore, according to another exemplary embodiment of the present invention, the radiation source may be adapted for emitting a polychromatic radiation beam.

According to another exemplary embodiment of the present invention, an image processing device for examination of an object of interest may be provided, the image processing device comprising a memory for storing image data and scatter data of the object of interest. Furthermore, the image processing device may comprise a correction unit adapted for correcting the image data on the basis of the scatter data, wherein the image data is detected at a first position of a focal spot of the electromagnetic radiation relative to the detector unit, and wherein the scatter data is detected at a second position of the focal spot relative to the detector unit, wherein the second position is different from the first position.

Therefore, an image processing device may be provided which is adapted for performing an improved scatter correction for, for example, a cone-beam computer tomography apparatus.

According to another exemplary embodiment of the present invention, a method of examination of an object of interest is provided, the method comprising the steps of emitting electromagnetic radiation to the object of interest, detecting image data and scatter data of the object of interest, and correcting the image data on the basis of the scatter data. The image data is detected at a first position of a focal spot of the electromagnetic radiation relative to the detector unit and the scatter data is detected at a second, different position of the focal spot relative to the detector unit.

According to another exemplary embodiment of the present invention, a computer-readable medium may be provided, in which a computer program of examination of an object of interest is stored which, when being executed by a processor, is adapted to carry out the above-mentioned method steps.

Furthermore, the present invention relates to a program element of examination of an object of interest, which may be stored on the computer-readable medium. The program element may be adapted to carry out the steps of emitting electromagnetic radiation to the object of interest, detecting image data and scatter data of the object of interest and correcting the image data on the basis of the scatter data.

The program element may preferably be loaded into working memories of a data processor. The data processor may thus be equipped to carry out exemplary embodiments of the methods of the present invention. The computer program may be written in any suitable programming language, such as, for example, C++ and may be stored on a computer-readable medium, such as a CD-ROM. Also, the computer program may be available from a network, such as the WorldWideWeb, from which it may be downloaded into image processing units or processors, or any suitable computers.

It may be seen as the gist of an exemplary embodiment of the present invention that a direct measurement of the scatter radiation is performed which is then used for a correction of image data contaminated by scattering. According to an exemplary embodiment of the present invention, the scatter radiation measurement may be performed by utilizing a 1-dimensional anti-scatter-grid and an X-ray tube with an electronic focal spot movement. This may provide for an improved scatter correction and may lead to an improved image quality.

These and other aspects of the present invention will become apparent from and elucidated with reference to the embodiments described hereinafter.

Exemplary embodiments of the present invention will be described in the following, with reference to the following drawings.

The illustration in the drawings is schematically. In different drawings, similar or identical elements are provided with the same reference numerals.

Figure 1:
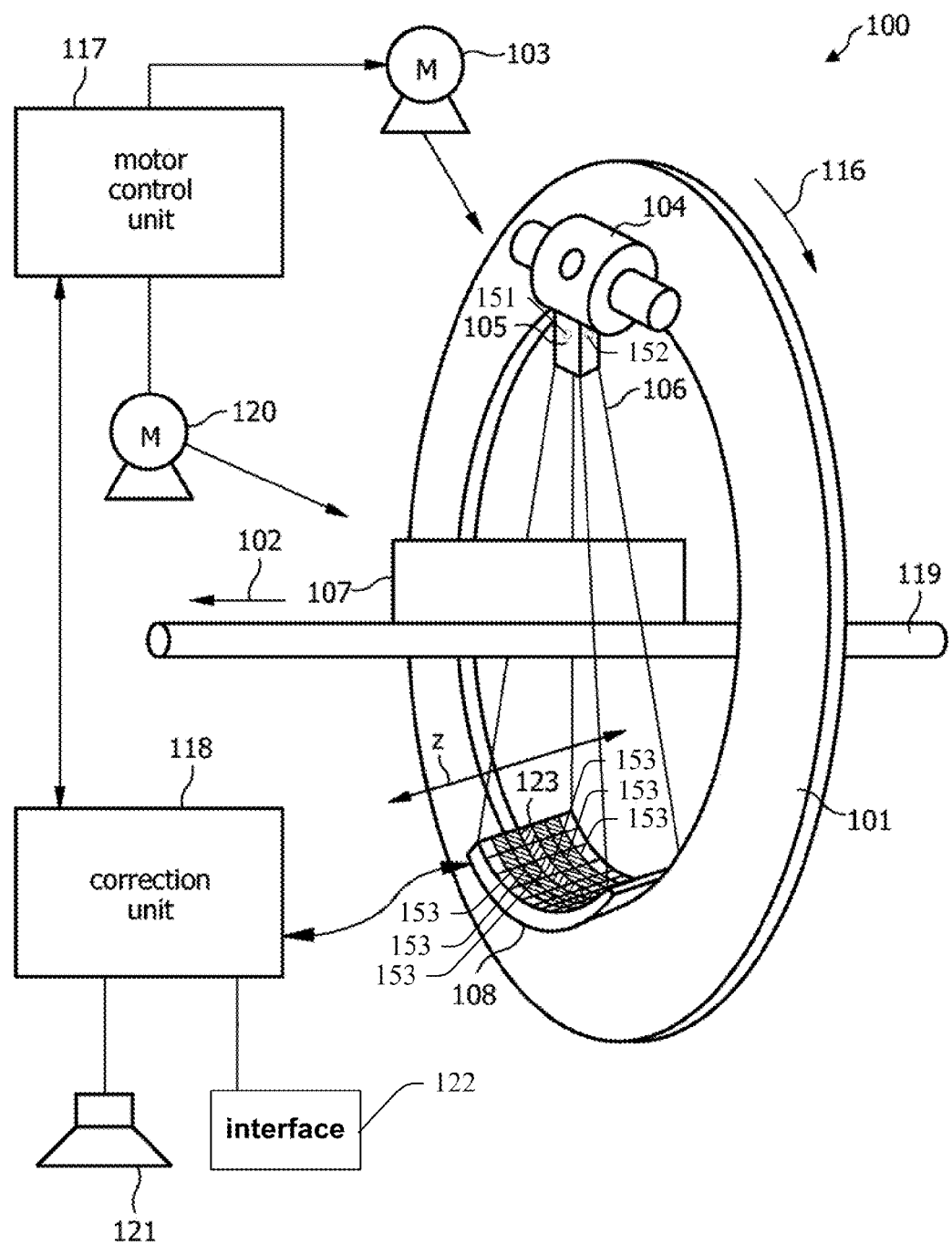
FIG. 1 shows a simplified schematic representation of an examination apparatus according to an exemplary embodiment of the present invention.

FIG. 1 shows an examination apparatus according to an exemplary embodiment of the present invention which is adapted as a computer tomography apparatus. With reference to this exemplary embodiment, the present invention will be described for the application in medical imaging. However, it should be noted that the present invention is not limited to this application, but may also be applied in the field of baggage inspection, or other industrial applications, such as material testing.

The computer tomography apparatus 100 depicted in FIG. 1 is a cone-beam CT scanner. The CT scanner depicted in FIG. 1 comprises a gantry 101, which is rotatable around a rotational axis 102. The gantry 101 is driven by means of a motor 103. Reference numeral 104 designates a source of radiation such as an X-ray source, which, according to an aspect of the present invention, emits a polychromatic radiation.

Reference numeral 105 designates an aperture system which forms the radiation beam emitted from the radiation source to a cone-shaped radiation beam 106. The cone-beam 106 is directed such that it penetrates an object of interest 107 arranged in the centre of the gantry 101, i.e. in an examination region of the CT scanner, and impinges onto the detector 108. As may be taken from FIG. 1, the detector 108 is arranged on the gantry 101 opposite to the source of radiation 104, such that the surface of the detector 108 is covered by the cone-beam 106. The detector 108, which is depicted in FIG. 1, comprises a plurality of detector elements 123 each capable of detecting, in an energy-resolving manner, X-rays or individual photons which have penetrated the object of interest 107.

During a scan of the object of interest 107, the source of radiation 104, the aperture system 105 and the detector 108 are rotated along the gantry 101 in the direction indicated by arrow 116. For rotation of the gantry 101 with the source of radiation 104, the aperture system 105 and the detector 108, the motor 103 is connected to a motor control unit 117, which is connected to a calculation or correction unit 118.

In FIG. 1, the object of interest 107 may be a patient or an item of baggage which is disposed on a conveyor belt 119. During the scan of the object of interest 107, while the gantry 101 rotates around the item of baggage 107, the conveyor belt 119 displaces the object of interest 107 along a direction parallel to the rotational axis 102 of the gantry 101. By this, the object of interest 107 is scanned along a helical scan path. The conveyor belt 119 may also be stopped during the scans to thereby measure single slices. Instead of providing a conveyor belt 119, for example, in medical applications where the object of interest 107 is a patient, a movable table may be used. However, it should be noted that in all of the described cases it may also be possible to perform other scan paths such as the saddle trajectory by moving the table periodically back and forth at twice the frequency of the source-detector arrangement.

The detector 108 may be connected to the calculation or correction unit 118. The correction unit 118 may receive the detection result, i.e. the read-outs from the detector elements 123 of the detector 108 and may determine a scanning result on the basis of the read-outs. Furthermore, the correction unit 118 communicates with the motor control unit 117 in order to coordinate the movement of the gantry 101 with motors 103 and 120 with the conveyor belt 119.

The correction unit 118 may be adapted for correcting image data on the basis of scatter data, wherein the image data is detected at a first position 150 of a focal spot of the electromagnetic radiation relative to the detector unit 108 and wherein the scatter data is detected at a second position 151 of the focal spot relative to the detector unit 108 which is different from the first position, according to an exemplary embodiment of the present invention. A reconstructed image generated by the correction unit 118 may be output to a display (not shown in FIG. 1) via an interface 122.

The correction unit 118 may be realized by a data processor to process read-outs from the detector elements 123 of the detector 108.

Furthermore, as may be taken from FIG. 1, the correction unit 118 may be connected to a loudspeaker 121, for example, to automatically output an alarm in case of the detection of suspicious material in the item of baggage 107.

The computer tomography apparatus 100 for examination of the object of interest 107 includes the detector 108 having the plurality of detecting elements 123 arranged in a matrix-like manner, each being adapted to detect X-rays. Furthermore, the computer tomography apparatus 100 comprises the determination unit or reconstruction unit 118 adapted for reconstructing an image of the object of interest 107.

The computer tomography apparatus 100 comprises the X-ray source 104 adapted to emit X-rays to the object of interest 107. The collimator 105 provided between the electromagnetic radiation source 104 and the detecting elements 123 is adapted to collimate an electromagnetic radiation beam emitted from the electromagnetic radiation source 104 to form a cone-beam. The detecting elements 123 form a multi-slice detector array 108. The computer tomography apparatus 100 may be configured as a medical imaging apparatus or baggage inspection apparatus.

Figure 2:
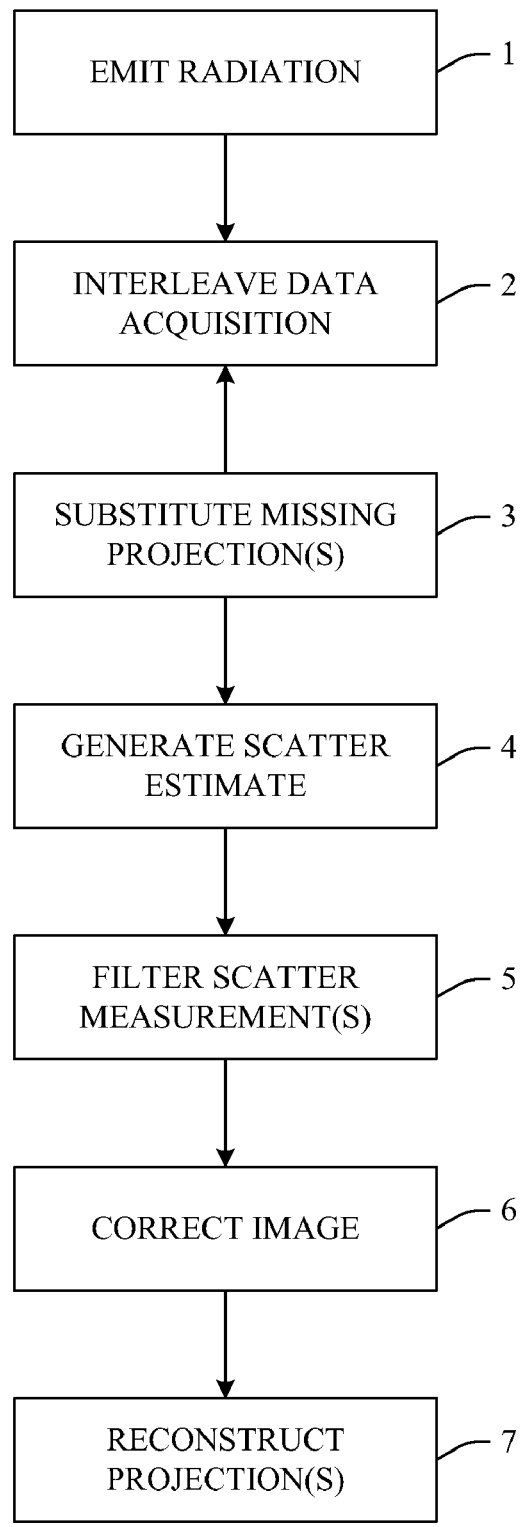
FIG. 2 shows a flow-chart of an exemplary method according to the present invention.

FIG. 2 shows a flow-chart of an exemplary method according to the present invention for directly measuring the scatter radiation and for using this measurement for a correction of the contaminated image data. The method starts at step 1 with the emission of electromagnetic radiation by a radiation source to the object of interest. Furthermore, a conventional CT scan is performed. Then, in step 2, the conventional data acquisition is interleaved with a scatter measurement by moving the focal spot such that no direct radiation hits the detector unit. The measuring of scatter data is performed by utilizing, for example, 1-dimensional anti-scatter-grid 153 and an X-ray tube with an electronic focal spot movement.

The conventional 1-dimensional anti-scatter-grid 153 may have anti-scatter-lamella along the Z-direction to reduce the scatter in the fan direction. For reducing the amount of direct radiation which reaches the detector unit, the focal spot may be moved for a scatter measurement such that no or only little direct radiation hits the detector. The resulting measurements may only contain scattered photons. Such a measurement may provide a good estimation of the scatter contribution to the imaging measurements.

In step 3, an interpolation may be performed in order to substitute the missing imaging projections. Furthermore, in step 4, an angular interpolation may be performed in order to generate a scatter estimate for each projection angle. Then, in step 5, a low-pass filtering may be performed on the scatter measurements.

After that, the image data may be corrected on the basis of the scatter data by a correction unit. This correction may be performed by subtracting the scatter measurements from the imaging measurements to generate a corrected projection.

Then, in step 7, a reconstruction may be performed with the corrected projections, resulting in a corrected image of the object of interest.

The invention makes use of the fact that scatter radiation may usually have only very small spatial variations. A relative small movement of the focal spot for a scatter measurement may have very little impact on the scatter compared to the imaging measurements. Therefore, the imaging measurements may be interleaved with scatter measurements. Since scatter may very slowly in the spatial domain, the scatter measurements may sporadically be interleaved in the image acquisition (for example according to a pre-determined sequence.

Figure 3:
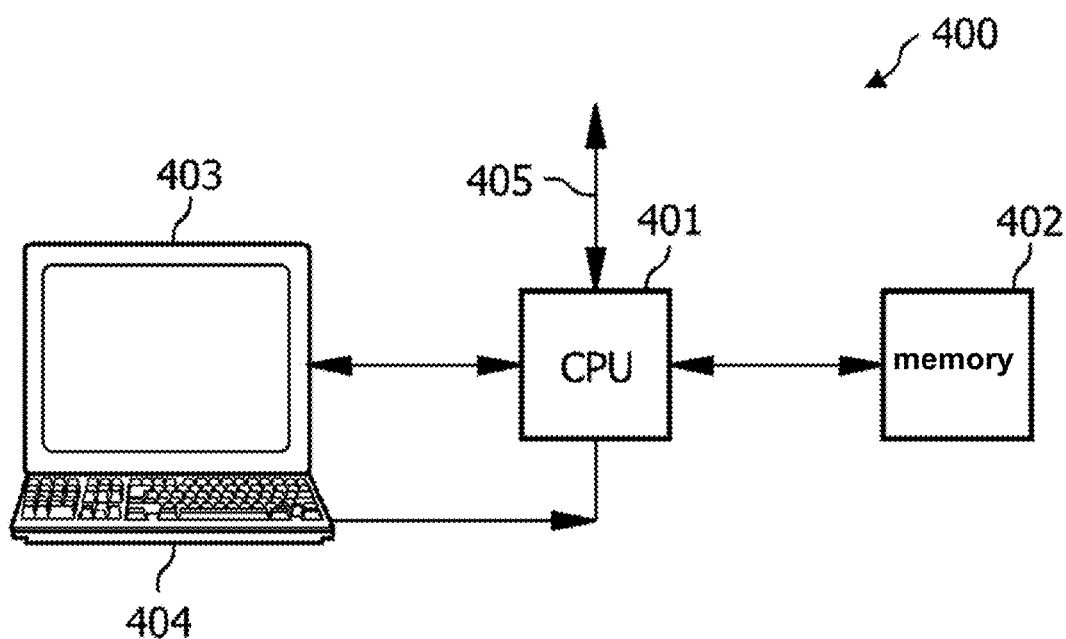
FIG. 3 shows an exemplary embodiment of an image processing device according to the present invention, for executing an exemplary embodiment of a method in accordance with the present invention.

FIG. 3 depicts an exemplary embodiment of a data processing device 400 according to the present invention for executing an exemplary embodiment of a method in accordance with the present invention. The data processing device 400 depicted in FIG. 3 comprises a central processing unit (CPU) or image processor 401 connected to a memory 402 for storing an image depicting an object of interest, such as a patient or an item of baggage. The data processor 401 may be connected to a plurality of input/output network or diagnosis devices, such as a CT device. The data processor 401 may furthermore be connected to a display device 403, for example, a computer monitor, for displaying information or an image computed or adapted in the data processor 401. An operator or user may interact with the data processor 401 via a keyboard 404 and/or other output devices, which are not depicted in FIG. 3.

Furthermore, via the bus system 405, it may also be possible to connect the image processing and control processor 401 to, for example, a motion monitor, which monitors a motion of the object of interest. In case, for example, a lung of a patient is imaged, the motion sensor may be an exhalation sensor. In case the heart is imaged, the motion sensor may be an electrocardiogram.

Exemplary embodiments of the invention may be sold as a software option to CT scanner console, imaging workstations or PACS workstations.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

The invention claimed is:

1. A computed tomography examination apparatus, comprising:
    a radiation source that rotates about a rotation axis along a z-direction and that emits electromagnetic radiation, which traverses an object of interest, alternately from a first focal spot at a first position and a second focal spot at a second different position;
    a detector unit, located opposite the radiation source across the rotation axis, that rotates in coordination with the radiation source and that detects and sporadically interleaves image data and scatter data corresponding to emitted radiation traversing the object of interest, wherein the detector unit detects the image data when the radiation is emitted from the first focal spot at the first position, and the detector unit detects the scatter data when the radiation is emitted from the second focal spot at the second position; and
    a correction component that corrects the image data on the basis of the scatter data.

2. The examination apparatus of claim 1, further comprising:
    an anti-scatter-grid adapted for filtering the electromagnetic radiation.

3. The examination apparatus of claim 2,
    wherein the anti-scatter-grid is a 1-dimensional anti-scatter-grid.

4. The examination apparatus of claim 2,
wherein the anti-scatter-grid is arranged between the object of interest and the detector unit.

5. The examination apparatus of claim 1,
wherein the image data comprises a first amount of direct radiation and a second amount of scatter radiation;
wherein the scatter data comprises a third amount of direct radiation and a fourth amount of scatter radiation;
wherein a first fraction of the first amount and the second amount is significantly bigger than a second fraction of the third amount and the fourth amount.

6. The examination apparatus of claim 1,
wherein the radiation source is adapted for electronically moving the focal spot from the first position to the second position.

7. The examination apparatus of claim 1,
wherein the image data is detected at a first time;
wherein the scatter data is detected at a second time; and
wherein the first time and the second time correspond to a detection sequence.

8. The examination apparatus of claim 1,
wherein the correction unit is further adapted for performing a first interpolation to substitute a missing imaging projection, wherein the first interpolation is not based upon a previous image reconstruction.

9. The examination apparatus of claim 1,
wherein the correction unit is further adapted for performing a second angular interpolation to generate a scatter estimate for each projection angle.

10. The examination apparatus of claim 1,
further adapted for directly performing a low pass filtering of the scatter data.

11. The examination apparatus of claim 1, configured as one of the group consisting of a baggage inspection apparatus, a medical application apparatus, a material testing apparatus and a material science analysis apparatus.

12. The examination apparatus of claim 1,
further comprising a collimator arranged between the electromagnetic radiation source and the detector unit;
wherein the collimator is adapted for collimating an electromagnetic radiation beam emitted by the electromagnetic radiation source to form a cone-beam.

13. The apparatus of claim 1, the detector unit, comprising:
a two-dimensional array of detector elements; and
a one-dimensional anti-scatter grid coupled thereto, wherein the one-dimensional anti-scatter grid rotates with the detector unit and the radiation source.

14. The apparatus of claim 13, the one-dimensional anti-scatter grid, comprising: anti-scatter lamella arranged along the z-direction, wherein the lamella block direct radiation when the second focal spot is at the second position.

15. The apparatus of claim 13, wherein no radiation shielding or blocking elements are inserted between the object of interest and the one-dimensional anti-scatter grid.

16. The apparatus of claim 15, further comprising an aperture that shapes the emitted radiation, wherein no radiation shielding or blocking elements are inserted between the aperture and the one-dimensional anti-scatter grid.

17. An image processing device for examination of an object of interest, comprising:
a memory for storing image data and scatter data of the object of interest detected with a tomographic imaging apparatus; and
a correction unit adapted for correcting the image data on the basis of the scatter data;
wherein the image data is detected with a rotating focal spot of the tomographic imaging apparatus at a first position, sporadically interleaved with the scatter data that is detected with the rotating focal spot at a second different position, wherein the image data and the scatter data are collected via a same rotation of the rotating focal spot;
wherein the correction unit is further adapted for performing at least one of a first interpolation to substitute a missing image projection, a second angular interpolation to generate a scatter estimate for each projection angle, and a low pass filtering of the scatter data.

18. A method of examination of an object of interest, comprising:
emitting from a focal spot of a rotating radiation source of a tomographic imaging apparatus electromagnetic radiation that traverse the object of interest;
detecting with a detector unit of the tomographic imaging apparatus rotating in coordination with the rotating radiation source image data and scatter data of the object of interest, wherein the image data is detected with the focal spot at a first position, sporadically interleaved with the scatter data that is detected with the focal spot at a second different position; and
correcting, by a correction unit, the image data on the basis of the scatter data.

19. A non-transitory computer-readable medium, in which a computer program of examination of an object of interest is stored which, when being executed by a processor, is adapted to carry out the steps of:
emitting, by a rotating radiation source, electromagnetic radiation to the object of interest;
detecting, by a detector unit rotating in coordination with the rotating radiation source, image data and scatter data of the object of interest, wherein the image data and the scatter data are detected in a common revolution of the rotating radiation source;
correcting, by a correction unit, the image data on the basis of the scatter data; and
performing at least one of a first interpolation to substitute a missing imaging projection, a second angular interpolation to generate a scatter estimate for each projection angle, and a low pass filtering of the scatter data;
wherein the image data is detected with a focal spot of the radiation source at a first position, sporadically interleaved with the scatter data that is detected with the focal spot at a second different position.

* * * * *